United States Patent [19]

Farng et al.

[11] Patent Number: 4,985,157
[45] Date of Patent: Jan. 15, 1991

[54] MIXED ALKOXYLATED ALCOHOL-HYDROQUINONE/RESORCINOL BORATES-ANTIOXIDANTS

[75] Inventors: Liehpao O. Farng, Lawrenceville; Andrew G. Horodysky, Cherry Hill; Robert E. Ernhoffer, Sewell; John A. Keller, Jr., Pitman, all of N.J.

[73] Assignee: Mobil Oil Corporation, Fairfax, Va.

[21] Appl. No.: 346,031

[22] Filed: May 1, 1989

[51] Int. Cl.$^5$ .................................... C10M 103/00
[52] U.S. Cl. ........................... 252/49.6; 252/32.7 E; 252/389.41; 558/286; 558/287; 558/291; 558/293; 558/294
[58] Field of Search .................. 252/49.6, 52 R, 42.7, 252/32.7 E, 49.6, 52 A, 389.41; 558/286, 287, 291, 293, 294

[56] References Cited

U.S. PATENT DOCUMENTS

| | | | |
|---|---|---|---|
| 2,053,474 | 9/1936 | Groves | 252/49.6 |
| 2,813,830 | 11/1957 | Trautman | 252/49.6 |
| 2,975,134 | 3/1961 | Cook | 558/291 |
| 2,984,550 | 5/1961 | Chamot | 44/62 |
| 3,316,287 | 4/1967 | Nunn, Jr. et al. | 558/294 |
| 4,440,556 | 4/1984 | Horodysky | 252/49.6 |
| 4,472,289 | 9/1984 | Horodysky et al. | 252/49.6 |
| 4,530,770 | 7/1985 | Broid | 252/49.6 |
| 4,600,517 | 7/1986 | Doner et al. | 252/52 R |
| 4,655,948 | 4/1987 | Doner et al. | 252/49.6 |
| 4,761,482 | 8/1988 | Karol | 252/47.5 |
| 4,780,227 | 10/1988 | Doner et al. | 252/49.6 |
| 4,781,850 | 11/1988 | Doner et al. | 252/49.6 |
| 4,788,340 | 11/1988 | Horodysky | 252/49.6 |
| 4,828,732 | 5/1989 | Doner | 252/32.7 E |
| 4,828,740 | 5/1989 | Farng et al. | 252/49.7 |

Primary Examiner—Margaret B. Medley
Attorney, Agent, or Firm—A. J. McKillop; C. J. Speciale; H. M. Flournoy

[57] ABSTRACT

Mixed alkoxylated alcohol-hydroquinone or alkoxylated alcohol-resorcinol borates are effective multifunctional antioxidants for lubricants.

30 Claims, No Drawings

MIXED ALKOXYLATED ALCOHOL-HYDROQUINONE/RESORCINOL BORATES-ANTIOXIDANTS

CROSS REFERENCE TO RELATED APPLICATIONS

This application is related to Ser. No. 078,949 filed Jul. 29, 1987, entitled Mixed Hydroquinone-Hydroxyester Borates As Antioxidants, now U.S. Pat. No. 4,828,740, and to Ser. No. 346,033 filed May 1, 1989 entitled Mixed Resorcinol-Hydroxyester Borates As Antioxidants now pending.

BACKGROUND OF THE INVENTION

This application is directed to novel additive products comprising mixed alkoxylated alcohol-hydroquinone or resorcinol borates which when incorporated into oils of lubricating viscosity or greases thereof provide superior lubricant compositions having excellent antioxidant activity and antiwear performance.

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode.

Antioxidants or oxidation inhibitors are used to minimize the effects of the oil deterioration that occurs. The degree and rate of oxidation will depend on temperature, air and oil flow rates and, of particular importance, on the presence of metals or contaminants that may catalytically promote oxidation. Antioxidants generally function by prevention of chain peroxide reaction and/or metal catalyst deactivation.

Water (moisture) is another critical problem. In spite of even extraordinary precautionary efforts, water is found as a film or in minute droplets in vessels containing various hydrocarbon distillates. This brings about ideal conditions for corrosion and damage of metal surfaces of the vessels and the materials contained therein. Also in the lubrication of internal combustion engines, for example, significant quantities of water are often present as a separate phase within the lubricating system. Another serious problem in respect to metallic surfaces in contact with adjacent metallic surfaces is wear caused by the contact of such surfaces.

One material capable of simultaneously and effectively coping with these and related problems is highly desirous. It has now been found that the use of these novel mixed hydroquinone or resorcinol-alkoxylated alcohol borates provides exceptional antioxidant, antiwear and corrosion inhibiting activity with potential antifatique, friction reducing, antirust and high temperature stabilizing properties.

The use of hydroquinone and resorcinol is well known because of their antioxidant properties in a variety of petroleum and non-petroleum products.

The use of borates has found extensive application in such diverse areas as grease additives, brake and hydraulic fluids, and fuel and combustion additives.

The use of alkoxylated alcohols or alkoxylated phenols has been widely reported as having beneficial multifunctional characteristics in a variety of fuel and lubricant applications.

It is an object of this invention to provide lubricant compositions of improved multifunctional capability, e.g., antioxidant, antiwear and antirust/anticorrosion characteristics. It is a further object to provide novel lubricant additive products derived from mixed alkoxylated hydroquinone or resorcinol borates.

SUMMARY OF THE INVENTION

This application is directed to lubricant products derived from mixed alkoxylated alcohol hydroquinone/resorcinol borates and to lubricant compositions containing small additive concentrations of mixed alkoxylated alcohol-hydroquinone/resorcinol borates or mixed alkoxylated alcohol-resorcinol borates. These novel compounds posses excellent antioxidant activity and multifunctional antiwear performance. Accordingly, this application is directed to the above referred to novel additives and to novel lubricant compositions containing same and to their use.

DESCRIPTION OF SPECIFIC EMBODIMENTS

A method by which the additive products in accordance with the invention may be prepared is outlined below. For example, triethoxylated mixed dodecanol-pentadecanol (commerically obtained from Shell Chemical Company as Neodol 25-3 triethoxylated mixed $C_{12}$–$C_{15}$ alcohols) was co-borated with hydroquinone or resorcinol to form mixed borate esters as generally described below:

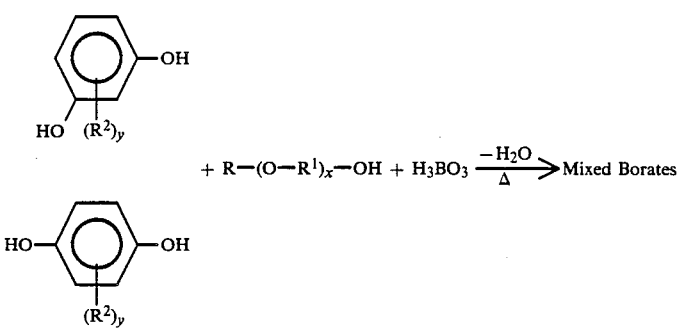

where R is $C_1$ to about $C_{30}$ hydrocarbyl, which includes but is not limited to aliphatic, cyclic, aromatic, and the like, and can optionally contain sulfur, nitrogen, phosphorus and/or oxygen, $R^1$ is $C_2$ to about $C_{20}$ hydrocarbyl, preferably $C_2$–$C_6$ hydrocarbyl, $R^2$ is $C_1$ to about $C_{30}$ hydrocarbyl, and can optionally contain sulfur, nitrogen, phosphorus and/or oxygen, x is an integer varying from 1 to about 20, and y is an integer varying from 0 to about 3, with 1–2 being preferred.

Both the hydroquinone and/or resorcinol moiety and the borate ester are believed to provide the basis for synergistic antioxidant activity. The alkoxylated alcohol and borate ester are also believed to contribute additional antirust, detergency and/or friction reducing properties to the additives. Although applicants do not wish to be held to a particular theory, these benefical properties are believed to be enhanced as a result of this novel internal synergism. This internal synergism concept is believed to be applicable to similar structures containing hydroquinone or resorcinol borate ester and alkoxylated alcohol or alkoxylated phenol moieties within the same molecule.

The alkoxylated alcohol usually contains at least six carbon atoms to about sixty carbon atoms. Preferred are such alcohols as dodecanol, pentadecanol and mixtures thereof.

Boric acid can be used as a boronating agent or metaborates, triakyl borates or any other suitable boronating agent may be employed. Suitable metaborates include but are not limited to trimethyl metaborate(trimethoxyboroxine), triethyl metaborate, tributyl metaborate. Suitable trialkyl borates include but are not limited to trimethyl borate, triethylborate, triisopropyl borate(triisopropoxyborane), tributyl borate(tributoxyborane), tri-tert-butyl borate.

The reaction conditions are not believed to be critical. Conditions therefore may vary widely, depending upon such as whether or not a solvent is used. Suitable solvents include hydrocarbon solvents such as toluene and the like. The pressure may generally be ambient or slightly higher if desired. The temperature may vary from ambient or about 35° C. to about 250° C. or reflux. An excess of one reagent or another can be used. Molar quantities, less than molar quantities, or more than molar quantities of boronating agent can be used. Up to a 500% molar excess of boronating agent can be used.

The additives may be incorporated into any suitable lubricating media which comprises oils of lubricating viscosity, e.g., mineral or synthetic; or mixtures of mineral and synthetic, or greases in which the aforementioned oils are employed as a vehicle or into such functional fluids as hydraulic fluids, brake fluids, power transmission fluids and the like. In general, mineral oils and/or synthetic oils, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800.

In instances where or synthetic oils are desired in preference to mineral oils as the vehicle for the grease, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

The products of this application also show good compatibility when used in the presence of other additives in the lubricant compositions. Therefore, fully formulated lubricating oils may include a variety of additives (for their known purpose) such as dispersants, detergents, inhibitors, antiwear agents, antioxidants, antifoam agents, pour depressants and other additives including phenates, sulfonates and phosphates such as zinc dithiophosphates, zinc dihydrocarbyl phosphorodithioates and ashless non-metallic dihydrocarbyl phosphorodithioates.

Where the lubricant is to be employed in the form of a grease, the lubricating oil is generally employed in an amount sufficient to balance the total grease composition, after accounting for the desired quantity of the thickening agent and other additive components to be included in the grease formulation.

When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above described additives, are combined with a grease forming quantity of a thickening agent. For this purpose, a wide variety of materials are dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolve when used at the required temperature within a particular environment. Soap thickeners such as metallic (lithium or calcium) soaps including hydroxy stearate and/or stearate soaps can be used. However, in all other respects, any material which is normally employed for thickening or gelling hydrocarbon fluids or forming greases can be used in preparing the aforementioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

Included among the other useful thickening agents are alkali and alkaline earth metal soaps of methyl-12-hydroxystearate, diesters of a $C_4$ to $C_{12}$ dicarboxylic acid and tall oil fatty acids. Other alkali or alkaline earth metal fatty acids containing from 12 to 30 carbon atoms and no free hydroxyl may be used. These include soaps of stearic and oleic acids.

As has been disclosed hereinabove, the reaction products are useful as multifunctional antiwear/antioxidant/antirust agents. They are added to the lubricating medium in amounts sufficient to impart such properties to the lubricant. More particularly, such properties will be imparted to the lubricant by adding from about 0.01% to about 10% by weight, preferably from about 0.05% to about 3%, of the neat product.

The following example is exemplary and is not intended as a basis for limitations.

EXAMPLE 1

Approximately 55 g hydroquinone, 61.8 g boric acid and 336 g of triethoxylated mixed dodecanol-pentadecanol (commerically obtained form Shell Chemical Company as Neodol 25-3) and 200 ml toluene were mixed in a reactor equipped with heater, stirrer and Dean-Stark trap. The reactants were heated at 125° C. over a period of six hours during which 41 g water was azeotropically collected. The mixture was filtered to remove solids and the volatiles were removed by distillation at reduced pressure. Approximately 358 g of product was recovered after distillation. The product contained approximately 2 weight percent boron.

The mixed alkoxylated alcohol-hydroquinone borates of the Example were blended into mixed mineral oils and evaluated for antiwear performance using the Four-Ball Wear Test (ASTM D2266) for further details see U.S. Pat. No. 4,761,482. As can be seen from the data in Table 1, the mixed alkoxylated alcohol-hydroquinone borates exhibit significant antiwear properties.

TABLE 1

| Four-Ball Wear Test (2000 rpm, 60 kg load, 30 min, 200° F.) ||
|---|---|
| Examples | Wear Scar Diameter, mm |
| Base oil (80% solvent paraffinic bright, 20% solvent paraffinic neutral mineral oils) | 3.34 |
| 1% of Example 1 in above base oil. | 1.02 |

The mixed alkoxylated alcohol-hydroquinone borates were blended into a ISO VG 220 lithium hydroxystearate thickened mineral oil base grease. Dropping point evaluation using ASTM D-2265 test method was performed using greases containing 1-3 wt % of the Example. As shown by the data in Table 2, the mixed borates of this patent information were found to significantly increase the dropping point of the grease.

TABLE 2

| Dropping Point Test, ASTM D-2265 ||
|---|---|
| Examples | Dropping Point, °F. |
| Lithium hydroxystearate thickened mineral oil derived grease | 410 |
| 1% of Example 1 above base grease | 487 |
| 2% of Example 1 above base grease | 505 |
| 3% of Example 1 above base grease | 517 |

The products of this invention exhibit very good multifunctional antioxidant, antiwear and high-temperature stabilizing properties especially under the severe conditions used in the performance screening tests. The products of this invention when used in premium quality automotive and industrial lubricants will significantly enhance stability and extend service life. The novel compositions described herein are useful at low concentrations and do not contain any potentially undesirable metals or chlorine and are ashless. These multifunctional antioxidants can be commercially made using an economically favorable one-step, one-pot condensation process which could be readily implemented using known technology in readily available equipment.

Although the present invention has been described with preferred embodiments, it is to be understood that modifications and variations may be utilized without departing from the spirit and scope of this invention, as those skilled in the art will readily understand. Such modifications and variations are considered to be within the purview and scope of the appended claims.

What is claimed is:

1. A composition comprising a major amount of an oil of lubricating viscosity or grease or other solid lubricant prepared therefrom and a minor multifunctional antioxidant/antirust/antiwear amount of from about 0.01 to about 10% by weight of the total composition of a mixed alkoxylated alcohol-hydroquinone or alkoxylated alcohol-resorcinol borate prepared as generally described below:

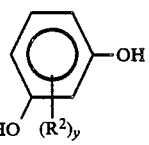

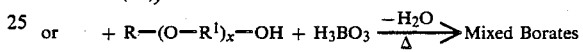

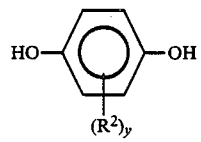

where R is $C_1$ to about $C_{30}$ hydrocarbyl, $R^1$ is $C_2$ to about $C_{20}$ hydrocarbyl or $C_2$ to about $C_{20}$ containing sulfur, nitrogen, phosphorus and/or oxygen, $R^2$ is $C_1$ to about $C_{30}$ hydrocarbyl or $C_2$ to about $C_{30}$ hydrocarbyl containing sulfur, nitrogen, phosphorus and/or oxygen, x is an integer varying from 1 to about 20, and y is an integer varying from 0 to about 3 and where a boronating agent other than boric acid is used, said boronating agent being selected from the group consisting of metaborates and trialkyl borates.

2. The composition of claim 1 where the alcohol is a mixed triethoxylated alcohol.

3. The composition of claim 1 where said alcohol is triethoxylated mixed dodecanol-pentadecanol.

4. The composition of claim 1 where the reactants are resorcinol, triethoxylated mixed dodecanol-pentadecanol and boric acid.

5. The composition of claim 1 where the reactants are hydroquinone, triethoxylated mixed dodecanol-pentadecanol and boric acid.

6. The composition of claim 1 where molar quantities, less than molar quantities or more than molar quantities of boronating agent are used.

7. The composition of claim 1 where said oil of lubricating viscosity is selected from mineral oils, synthetic oils and mixtures thereof.

8. The composition of claim 7 where said oil is a mineral oil.

9. The composition of claim 7 where said oil is a synthetic oil.

10. The composition of claim 7 where said oil is a mixture of synthetic and mineral oils.

11. The composition of claim 1 where said composition is a grease composition.

12. The composition of claim 11 where said grease is synthetic and/or mineral oil lithium complex thickened grease.

13. A product of reaction made by reacting (1) a hydrocarbyl substituted hydroquinone or resorcinol with (2) an alkoxylated alcohol or mixture of alkoxylated alcohols and (3) a boronating agent as generally described below:

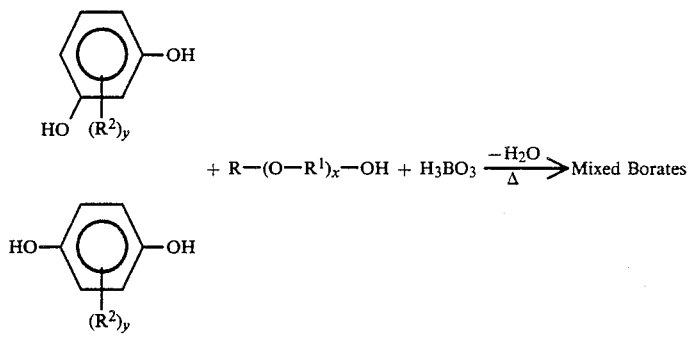

where R is $C_1$ to about $C_{30}$ hydrocarbyl, $R^1$ is $C_2$ to about $C_{20}$ hydrocarbyl $C_2$ to about $C_{20}$ hydrocarbyl containing sulfur, nitrogen, phosphorus and/or oxygen, $R^2$ is $C_1$ to about $C_{30}$ hydrocarbyl or $C_2$ to about $C_{30}$ hydrocarbyl containing sulfur, nitrogen, phosphorus and/or oxygen, x is an integer varying from 1 to about 20, and y is an integer varying from 0 to about 3.

14. The product of claim 13 where said reactants are resorcinol, triethoxylated mixed dodecanol-pentadecanol and boric acid.

15. The product of claim 13 where said reactants are hydroquinone, triethoxylated mixed dodecanol-pentadecanol and boric acid.

16. The product of claim 13 where in said process, the boronating agent is selected from the group consisting of boric acid, metaborates or trialkyl borates.

17. A process of preparing mixed alkoxylated alcohol-hydroquinone/resorcinol borates suitable from use as multifunctional antioxidant/antirust/antiwear lubricant additives comprising reacting (1) a $C_1$-$C_{30}$ hydrocarbyl hydroquione or resorcinol (2) an alkoxylated alcohol having the following generalized structure R—(O-$R^1$)$_x$—OH where R is $C_1$ to about $C_{30}$ hydrocarbyl, and $R_1$ is $C_2$ to about $C_{20}$ hydrocarbyl or $C_2$ to about $C_{20}$ hydrocarbyl containing sulfur, nitrogen, phosphorus and/or oxygen, and where x is an integer varying from 1 to about 20 or mixture thereof and (3) a boronating agent, said reaction being carried out at temperatures varying from 35° to about 250° C. at ambient or slightly higher pressure with molar quantities, less than molar quantities and more than molar quantities of said boronating agent.

18. The process of claim 17 where the boronating agent is selected from the group consisting of boric acid, metaborates, and trialkyl borates.

19. The process of claim 18 where the boronating agent is boric acid.

20. The process of claim 17 where reactant (1) is resorcinol or hydrocarbyl substituted resorcinol.

21. The process of claim 17 where reactant (1) is hydroquinone or hydrocarbyl substituted hydroquinone.

22. The process of claim 17 where the alkoxylated alcohol is mixed triethoxylated dodecanol-pentadecanol.

23. The process of claim 17 where the reactants are (1) hydroquinone, (2) triethoxylated mixed dodecanol-pentadecanol, and (3) boric acid.

24. The process of claim 17 where the reactants are (1) resorcinol, (2) triethoxylated mixed dodecanol-pentadecanol and (3) boric acid.

25. The process of claim 17 where said process is a one pot, one-step process.

26. A process for improving the fuel economy of an internal combustion engine, comprising contacting the moving parts of said engine with a composition as described in claim 1.

27. A process for improving the dropping point, and/or oxidative stability of a metal or non-metal hydroxyl containing soap thickened grease by blending therein a minor amount of from about 0.1 to about 10% by weight of the total composition of an additive product as described in claim 13.

28. The composition of claim 1 containing as an additional additive component a minor effective antiwear-/extreme pressure amount of a phosphorus and/or sulfur containing product.

29. The composition of claim 28 where the additional component is a phosphorodithioate.

30. The composition of claim 29 where said phosphorodithioate is a zinc dihydrocarbyl phosphorodithioate or an ashless non-metallic dihydrocarbyl phosphorodithioate.

* * * * *